United States Patent [19]

Takahashi

[11] 4,080,212

[45] Mar. 21, 1978

[54] DENTAL REMEDY FOR VITAL PULP COVERING AND ROOT CANAL FILLING, AND PREPARATION METHOD THEREFOR

[76] Inventor: Tadakazu Takahashi, 3-4-12, Zaimokuza, Kamakura, Kanagawa, Japan

[21] Appl. No.: 700,576

[22] Filed: Jun. 28, 1976

[30] Foreign Application Priority Data

Jun. 30, 1975 Japan ............................. 50-80665

[51] Int. Cl.$^2$ .................... C09K 3/00; C08G 8/04; C08G 8/08
[52] U.S. Cl. ................................ 106/35; 260/38; 260/40 R; 260/51 R; 260/52; 260/54; 260/57 R; 260/57 A; 260/57 C
[58] Field of Search .......... 106/35; 260/51 R, 57 R, 260/57 A, 38 R, 40 R, 54, 52

[56] References Cited

U.S. PATENT DOCUMENTS

| | | | |
|---|---|---|---|
| 2,413,294 | 12/1946 | Curtis | 106/35 |
| 2,516,438 | 7/1950 | Wheeler | 106/35 |
| 3,047,408 | 7/1962 | Dougherty | 106/35 |
| 3,266,147 | 8/1966 | Goldman | 106/35 |
| 3,929,493 | 12/1975 | Lee, Jr. et al. | 106/35 |

FOREIGN PATENT DOCUMENTS

| | | | |
|---|---|---|---|
| 7,104,757 | 5/1971 | Japan | 106/35 |
| 7,505,513 | 3/1975 | Japan. | |
| 110,154 | 8/1918 | United Kingdom | 106/35 |
| 134,757 | 11/1919 | United Kingdom | 106/35 |
| 165,758 | 7/1921 | United Kingdom | 106/35 |

*Primary Examiner*—Herbert J. Lilling
*Attorney, Agent, or Firm*—Ostrolenk, Faber, Gerb & Soffen

[57] ABSTRACT

An improved dental remedy used for vital pulp covering and root canal filling, and the preparation method therefor, in which the remedy is free from discoloration, excellent in disinfecting effect and adequate in the length of pot life before curing. The preparation method comprises the steps of: reacting formaldehyde or its polymer with phenol compounds and an alcohol-soluble vegetable oil or the interesterification product of a vegetable oil and a polyhydric alcohol; then stopping the reaction; leaving the reaction product standing still to cool; collecting oily material that has settled; rinsing and drying the oily material; and kneading the dried oily material with calcium oxide powder with or without X-ray contrast medium.

9 Claims, No Drawings

DENTAL REMEDY FOR VITAL PULP COVERING AND ROOT CANAL FILLING, AND PREPARATION METHOD THEREFOR

BACKGROUND OF THE INVENTION

1. Field of the Invention

This invention relates to an improved dental remedy which is used for vital pulp covering and root canal filling, and the preparation method therefor.

2. State of the Prior Art

The inventor of this application has made eager and extensive studies in the technical field concerned for many years. The outcomes of the studies have been disclosed in the patent specifications of Japanese Patent Publication Nos. Sho. 29-8197/1954 (Patent No. 212,303), Sho. 45-39834/1970 (Patent No. 637,507), Sho. 46-4757/1971 (Patent No. 621,124) and Sho. 50-5513/1975.

In brief, the method for preparing the dental remedy disclosed in the above patent specifications comprises the steps of: reacting formaldehyde and phenol compounds such as guaiacol with the addition of an alcohol-soluble vegetable oil or an interesterification product of a vegetable oil and a polyhydric alcohol to obtain an oily, millet jelly-like intermediate condensate; separating and rinsing the oily product (thus obtained product will be hereinafter referred to simply as "intermediate condensate"); and immediately before use, kneading the intermediate condensate by adding the powder of pure calcium hydroxide or calcium oxide and a smaller amount of x-ray contrast medium.

Several disadvantages caused in the conventional method have been obviated by degrees in the methods as disclosed in the foregoing patent specifications, however, they are not yet complete. That is, when the refined intermediate condensate obtained through the above method is kneaded with the powder mainly containing calcium hydroxide or calcium oxide and the kneaded mixture is used for treatment, it is subject to slight coloration after the lapse of long period of time. Though the dental remedy is more desirable as compared with the conventional ones, it is still slightly irritable, which property is clinically acceptable but somewhat defective in view of pathological results.

Further, in the method as disclosed in Japanese Patent Publication No. Sho. 50-5513/1975, the tendency for kneaded material to cure too rapidly has been eliminated by kneading the intermediate condensate with the powder mainly containing calcium oxide. By replacing calcium hydroxide with calcium oxide, the pot life of the kneaded material before curing can be made long and proper, for example, 20 to 30 minutes. However, the defect for the filled material to color after the lapse of a long time has not yet been removed.

SUMMARY OF THE INVENTION

In order to eliminate the above-mentioned disadvantage, the object of the present invention is to provide an improved dental remedy for vital pulp covering and root canal filling which is free from the coloration or staining after the remedy is applied to the teeth.

Further object of the present invention is to provide an improved method for preparing such a dental remedy without difficulty.

According to the method for preparing the dental remedy of the present invention, formaldehyde or its polymer is allowed to react on phenol compounds such as guaiacol, creosote and eugenol and alcohol-soluble vegetable oil or the interesterification product of a vegetable oil and a polyhydric alcohol in the presence of the catalyst of one or more of bi- or trifunctional organic acids and the catalyst promotor of organic acids other than the above ones, inorganic acids or their salts, thereby forming an oily intermediate condensate. The oily intermediate condensate is then settled, separated and rinsed with water to refine it. Before use for dental treatment, it is kneaded into a paste with the powder containing calcium oxide that is made by calcining calcium hydroxide solely or a mixture of calcium hydroxide and X-ray contrast media such as zinc oxide and barium sulfate.

DETAILED DESCRIPTION OF THE INVENTION

In the following, the present invention will be described in more detail.

The phenol compounds used in the present invention are exemplified by guaiacol, creosote, cresol, eugenol and resorcinol, of which guaiacol and eugenol are the most suitable and effective. Formaldehyde may, of course, be used in the form of paraformaldehyde. The alcohol-soluble vegetable oil used in the present invention is castor oil or the like, while the vegetable oils used for the preparation of interesterification products that are employed in the condensation of the present invention, are castor oil, soybean oil, peanut oil and olive oil. Exemplified as the polyhydric alcohols for the preparation of interesterification products are glycerol, polyethylene glycol and propylene glycol. In the interesterification, approximately equivalent amounts of the above-mentioned oil and polyhydric alcohol are allowed to react at about 230° C for 2 to 3 hours by heating in the presence of about 0.1 to 1.0% (as solid) of the catalyst such as calcium soap, zinc soap or zinc oxide. Of the interesterification products obtained in the above reaction, the monoglyceride is preferable to the diglyceride for the purpose of this invention, however, the occurrence of the diglyceride as an impurity does not cause any undesirable effect.

As the catalysts for the condensation of phenol and aldehydes in the conventional art, inorganic acids and their salts such as boric acid, sulfuric acid, phosphoric acid, acid sulfates, hyposulfites and sodium chloride, and organic acids and their salts such as acetic acid and zinc acetate have been used. With these catalysts, several defects occur, however, bi- or tri-functional organic acids, especially, oxalic acid, tartaric acid and citric acid are employed as the catalysts in the method of the present invention, therefore the disadvantages in the prior art can be successfully eliminated. That is, the aforementioned long-standing problem of coloration as the final defect can be completely solved by the use of the phenolformaldehyde intermediate condensate that is prepared in the presence of the catalyst of bi- or trifunctional organic acids, and even after the lapse of a long period of time, no coloration takes place. In addition, the present invention provides such advantages that the disinfecting effect of the obtained composition is satisfactory, and gives no disagreeable feeling of irritation to patients, and when the intermediate condensate of the present invention is kneaded with the powder composition mainly consisting of calcium oxide before use, the pot life of the mixture to cure is 20 to 30 minutes which fact is sufficient and desirable for practical uses.

In order that those skilled in the art may better understand the present invention and the manner in which it may be practised, the following specific examples are given.

EXAMPLES 1 – 8

The materials used for the preparation of the intermediate condensates of the present invention are shown in the following Table 1. In Examples 1, 2, 5 and 6, the molar ratios of guaiacol to formaldehyde are 1:0.8, and in the other examples, the ratios are 1:1.

Table 1

| Materials | Units | 1 | 2 | 3 | 4 | 5 | 6 | 7 | 8 |
|---|---|---|---|---|---|---|---|---|---|
| Phenol compound | | | | | | | | | |
| Guaiacol | g | 100 | 100 | 100 | 100 | 100 | 100 | 100 | 100 |
| Aldehydes | | | | | | | | | | |
| Paraformaldehyde | g | 20 | — | 25 | — | 20 | — | 25 | — |
| Formalin | g | — | 55 | — | 65 | — | 55 | — | 65 |
| Additives | | | | | | | | | |
| Alcohol-soluble vegetable oil or ester-interchanged vegetable oil | ml | 15–20 | 15–20 | 15–20 | 15–20 | 15–20 | 15–20 | 15–20 | 15–20 |
| Solvent | | | | | | | | | |
| Water | ml | 30–50 | — | 30–50 | — | 30–50 | — | 30–50 | — |
| Catalysts | | | | | | | | | |
| Oxalic acid | g | 0.5–2.0 | 0.5–2.0 | 0.5–2.0 | 0.5–2.0 | 0.5–2.0 | 0.5–2.0 | 0.5–2.0 | 0.5–0.2 |
| Citric acid | g | — | — | — | — | 2–4 | 2–4 | — | — |
| Tartaric acid | g | — | — | — | — | — | — | 2–4 | 2–4 |
| Catalyst promotors | | | | | | | | | |
| Acetic acid | ml | 1–2 | 1–2 | 1–2 | 1–2 | 1–2 | 1–2 | 1–2 | 1–2 |
| Sulfuric acid (10%) | ml | 2–5 | 2–5 | 2–5 | 2–5 | 2–5 | 2–5 | 2–5 | 2–5 |

Each mixture of the foregoing materials is allowed to react at about 90° C for 1 to 1.5 hours with stirring. When the reaction product becomes viscous like starch syrup, the reaction is stopped. The viscosity of the thus obtained reaction product is generally 50,000 to 70,000 cps. The addition of an alcohol-soluble vegetable oil or ester-interchanged vegetable oil may be done in the initial or intermediate stage of the reaction. Further, when 15 to 20 ml of 70% ethanol is added in two or three divided parts during the reaction, a desirable result may be obtained. The reaction product is then left to stand still and cool, where oily material will separate at the bottom. Then, only the oily material is collected, and refined by rinsing with water. After that, the obtained material is dried to form the intermediate condensate of the present invention.

The intermediate condensate obtained through the above procedure is stored in a container against the access of air, moisture and light.

In the meantime, the mixture of calcium oxide and X-ray contrast media is prepared with the following composition:
Calcium hydroxide: 20 – 90 g (preferably about 50 g)
Zinc oxide: about 20 g
Barium sulfate: about 30 g.
Calcium hydroxide solely or the above-mentioned mixture is calcined in air at a temperature of 540° C to 750° C so as to change the calcium hydroxide into calcium oxide, which is to be preserved in a sealed condition. This calcined material will be hereinafter referred to as "active calcium agent".

When the composition of the present invention is used, the above intermediate condensate and the above active calcium agent are kneaded together into a paste. In this step, if thoroughly dried zinc stearate is added to the composition, the active calcium agent is prevented from settling and, in addition, the stearate serves also as X-ray contrast medium. The exemplar formula for the composition of the present invention is as follows:

A. Active calcium agent (before calcination)
Calcium hydroxide: 20 – 90 g
Zinc oxide: 20 g
Barium sulfate 30 g.

B. Liquid agent
Intermediate condensate of the present invention: 20 – 60 ml
Castor oil or the above ester-interchanged oil: 10 ml
Propylene glycol: 40 ml
Absolute ethanol: 10 ml.

As disclosed above, 10 to 20 g of zinc stearate is further added when the composition is kneaded. The barium salts and zinc salts are gradually absorbed by the body after dental treatment.

The above formula is one instance for the remedy of the present invention, however, in the case that the calcium oxide absorbs carbon dioxide or moisture, the desirable therapeutic effect cannot be expected. The calcium oxide is much diluted with X-ray contrast medium and the intermediate condensate of the present invention, and the pot life of the kneaded composition is extended, thus the reaction against the living body is slowed down to facilitate dental treatment. When sufficient care is taken to avoid moistening, the active calcium agent can be kneaded into a paste by using some components of the above liquid agent such as castor oil and a part of propylene glycol, therefore, the mixing and kneading immediately before the use can be accomplished easily.

When the kneaded composition is used for filling in the preparation of vital tooth, covering of the dental pulp in vital pulpectomy or filling of an infected root canal, the composition exerts excellent effects on dental pulp and dental root tissue in the treatment, and a disinfecting effect satisfactory to prevent the treated tooth from secondary infection. Therefore, it will be understood that the dental remedy of the present invention is most suitable for the tretment and disinfection of dental diseases and for covering pulp tissue in vital pulpectomy.

Further, the bonding between the dental remedy of the present invention and dental tissue is made by the gradual penetration of the remedy into fine tubules of dentine through the action of calcium ion exchange. At the same time, the intermediate condensate of the present invention cures by itself and becomes firm. Accordingly, the microbes invading into the dentinal tubules are killed or firmly sealed up so as not to come out, and thus the secondary infection can be completely prevented.

Although the present invention has been described in connection with preferred examples thereof, many variations and modifications will now become apparent to those skilled in the art. It is preferred, therefore, that the present invention be limited not by the specific disclosure herein but only by the appended claims.

What is claimed is:

1. A method for preparing a dental remedy for vital pulp covering and root canal filling, which method comprises the steps of:
   A. reacting at about 90° C formaldehyde or paraformaldehyde with at least one phenol compound selected from the group consisting of guaiacol, creosote, cresol, eugenol and resorcinol and an alcohol-soluble vegetable oil or the interesterification product of a vegetable oil and a polyhydric alcohol which is at least one member selected from the group consisting of glycerol, polyethylene glycol and propylene glycol in the presence of the catalyst of one or more of bi- or tri-functional organic acids and catalyst promotor of one or more of organic acids other than said organic acids, inorganic acids and their salts;
   B. then stopping said reaction when a viscous intermediate condensate is produced;
   C. cooling the reaction product, whereby an oily material separates therefrom;
   D. collecting the oil material;
   E. rinsing said oily material with water to refine;
   F. drying said refined oily material; and
   G. kneading into a paste said dried oily material with an active calcium agent immediately before use wherein said active calcium agent is the material which is prepared by calcining calcium hydroxide solely or a mixture of calcium hydroxide and one or more body absorable X-ray contrast media, said calcium hydroxide being converted into calcium oxide through said calcination.

2. A method for preparing a dental remedy for vital pulp covering and root canal filling as claimed in claim 1, wherein said bi- or tri-functional organic acid is at least one member selected from the group consisting of oxalic acid, tartaric acid and citric acid.

3. A method for preparing a dental remedy for vital pulp covering and root canal filling as claimed in claim 1, wherein said alcohol-soluble vegetable oil is castor oil and said other vegetable oil used for preparing said interesterification product is at least one member selected from the group consisting of castor oil, soybean oil, peanut oil and olive oil.

4. A method for preparing a dental remedy for vital pulp covering and root canal filling as claimed in claim 1, wherein said reaction in step A is performed for 1 to 1.5 hours with stirring.

5. A method for preparing a dental remedy for vital pulp covering and root canal filling as claimed in claim 1, wherein said interesterification product is prepared under the reaction conditions of a temperature at about 230° C and a reaction time of 2 to 3 hours in the presence of about 0.1 to 1.0% (as solid) of the catalyst of calcium soap, zinc soap or zinc oxide.

6. A dental remedy for vital pulp covering and root canal filling which is prepared according to the method of claim 1.

7. An intermediate condensate for preparing the dental remedy for vital pulp covering and root canal filling, which condensate is prepared through the steps of A to F as claimed in claim 1.

8. A method of preparing a dental remedy for vital pulp covering and root canal filling as claimed in claim 1, wherein said X-ray contrast media is a zinc or barium salt.

9. A method of preparing a dental remedy for vital pulp covering and root canal filling as claimed in claim 1, wherein said phenol compound is guaiacol.

* * * * *